United States Patent

Gelbein et al.

[11] 4,051,140
[45] Sept. 27, 1977

[54] PREPARATION OF PYRIDINES AND NICOTINONITRILE FROM PIPERIDINES

[75] Inventors: Abraham P. Gelbein, Plainfield, N.J.; Paul Janssen, deceased, late of Bensberg-Refrath, Germany, by Almuth Janssen, heir; Hermann Richtzenhain, Much-Schwellenbach, Germany

[73] Assignee: The Lummus Company, Bloomfield, N.J.

[21] Appl. No.: 701,693

[22] Filed: July 1, 1976

[51] Int. Cl.² .................. C07D 213/24; C07D 213/57
[52] U.S. Cl. .............................. 260/290 P; 260/294.9
[58] Field of Search ........................ 260/290 P, 294.9

[56] References Cited

U.S. PATENT DOCUMENTS

| 3,555,021 | 1/1971 | Beutel et al. ............ 260/250 BN |
| 3,925,447 | 12/1975 | Gelbein ..................... 252/464 |

*Primary Examiner*—Alan L. Rotman
*Attorney, Agent, or Firm*—Marn & Jangarathis

[57] ABSTRACT

A piperidine, such as methyl piperidine is converted to the corresponding pyridine by the use of a supported vanadia catalyst. Nicotinonitrile can be produced by conversion of 3-methyl piperidine to 3-methyl pyridine with a supported vanadia catalyst, followed by ammonolysis to nicotinonitrile by the use of a supported vanadia catalyst.

11 Claims, 1 Drawing Figure

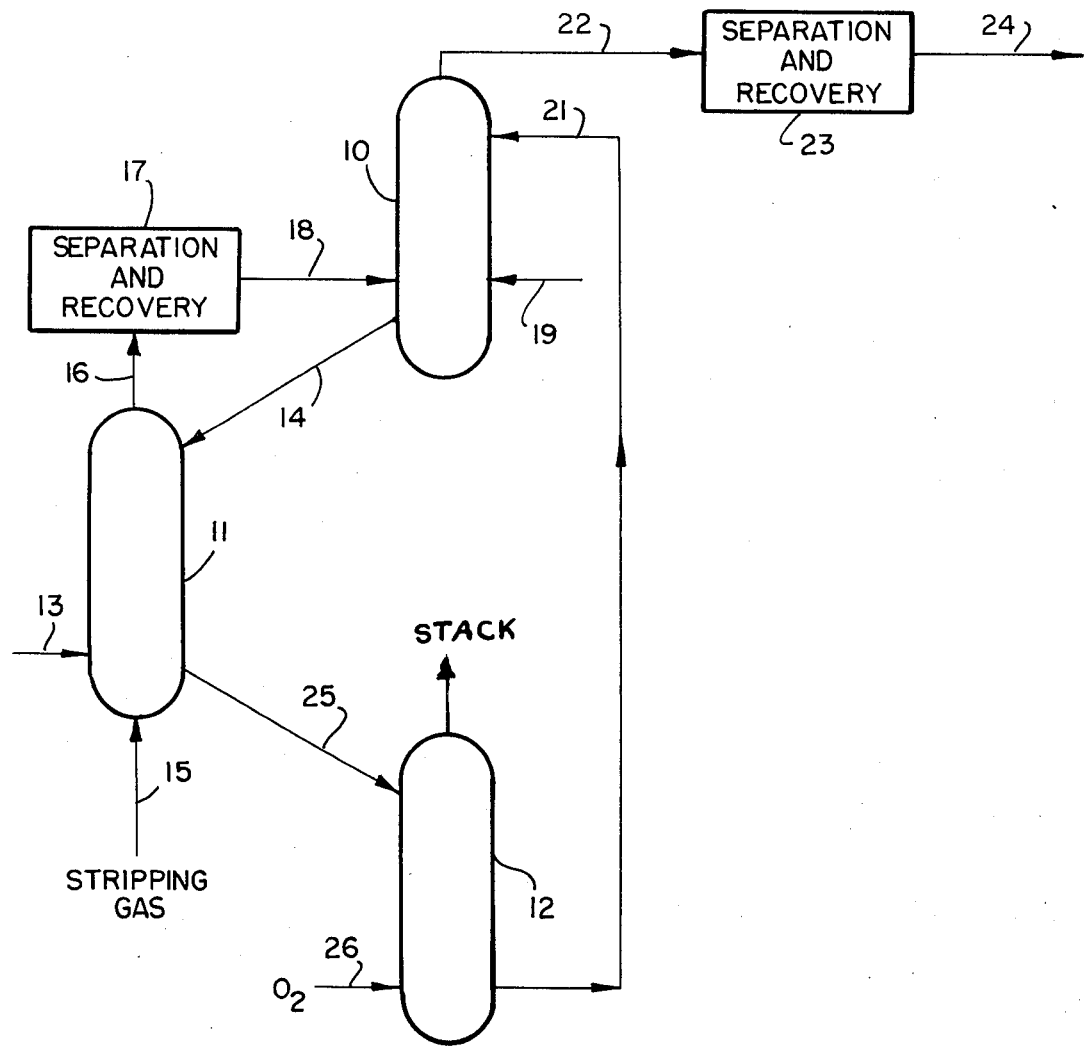

PREPARATION OF PYRIDINES AND NICOTINONITRILE FROM PIPERIDINES

This invention relates to the conversion of a piperidine to the corresponding pyridine. This invention further relates to the production of nicotinonitrile from a piperidine.

U.S. Pat. No. 3,555,021 discloses a process for the oxydehydrogenation of alkyl substituted heterocyclic compounds by the use of vanadia of molybdena chemically combined with cobalt, vanadium or molybdenum. The patent further discloses that attempts to use vanadium pentoxide for conversion of alkyl substituted heterocyclic compounds resulted in cleavage of the alkyl substiutents.

In accordance with the present invention, it has been found that alkyl substituted piperidines can be converted to the corresponding alkyl substituted pyridine by the use of a supported vanadia catalyst.

In accordance with another aspect of the present invention, an alkyl substituted piperidine is converted to the corresponding alkyl substituted pyridine by the use of a supported vanadia catalyst, followed by ammonolysis of the alkyl substituted pyridine to nicotinonitrile by use of a supported vanadia catalyst.

More particularly, the supported vanadia catalyst which is employed for effecting the conversion of a piperidine may be any one of the wide variety of supported vanadia catalysts which are conventionally employed for oxidation reactions. As known in the art, the vanadia may be supported on any one of a wide variety of supports, such as, silica, silica-alumina, the various forms of alumina, clay, anatase, and the like. The vanadia employed as the catalyst may be in the oxidized state or in one of its reduced states; i.e., the valence state of the vanadia may be +5 or less. In the case where vanadia in a +5 valence state is employed, the reaction proceeds by an oxydehydrogenation mechanism, with the vanadia being converted to a reduced state. In the reduced state, the piperidine is converted by a dehydrogenation mechanism. The oxydehydrogenation and dehydrogenation mechanisms for effecting conversion of a piperidine to a pyridine is represented by the following equations, employing methyl piperidine as a representative starting material:

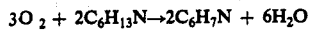

It is to be understood that oxygen could also be introduced into the reaction, in which case, the vanadia is maintained in its oxidized state, whereby the piperidine is continuously converted by an oxydehydrogenation mechanism. In accordance with the preferred embodiment, the reaction is effected in the absence of molecular oxygen.

The supported vanadia catalyst may be employed as a fixed bed or as a fluidized bed, with a fluidized bed being preferred. It is to be understood, however, that the reaction could be effected other than with a fixed or fluidized bed of catalyst.

The piperidine is converted to the corresponding pyridine at temperatures in the order of from about 500° F to about 1000° F, preferably in the order of from about 700° F to about 900° F.

The starting materials employed in the present invention are alkyl substituted piperidines. The substituted piperidines are generally alkyl substituted piperidines with the alkyl groups having from 1 to 5 carbon atoms, with the ring being substituted with one or more such alkyl groups. As representative examples of such starting materials, there may be mentioned: 2-, 3-, and 4-methyl piperidine, 2-, 3-, and 4-ethyl piperidine, 2,3-dimethyl piperidine, 2-methyl-5-ethyl piperidine, 2,4-dimethyl pyridine, 2,5-dimethyl piperidine, and the like.

The supported vanadia catalyst, which is employed for converting alkyl piperidine to the corresponding alkyl pyridine, is periodically treated to remove foulants therefrom. As known in the art, such foulants may be conveniently removed by contacting the catalyst with oxygen; for example, as air, at an elevated temperature. In general, such temperatures are in the order of from about 500° F to about 1200° F; however, it is to be understood that such temperatures are merely illustrative of those generally employed for effecting regeneration of the catalyst. Such regeneration of the catalyst by contacting with oxygen also effects oxidation of the vanadia to a higher valent state, whereby the supported vanadia catalyst, subsequent to the regeneration, initially catalyzes the conversion of a piperidine to the corresponding pyridine by an oxydehydrogenation mechanism. The vanadia is reduced in effecting such conversion and, accordingly, subsequently functions to catalyze the conversion of a piperidine to a pyridine by a dehydrogenation mechanism.

The ability to employ supported vanadia to catalyze the conversion of an alkyl piperidine to an alkyl pyridine by both an oxydehydrogenation and a dehydrogenation mechanism can be advantageous employed to provide heat requirements for such conversion. Thus, the oxydehydrogenation mechanism is an exothermic conversion, whereas the dehydrogenation mechanism is an endothermic conversion. As a result, by initially effecting the conversion with vanadia in an oxidized state, the heat released during the exothermic oxydehydrogenation can be employed for meeting heat requirements for the endothermic dehydrogenation mechanism. In such an embodiment, the supported vanadia catalyst would be continuously circulated between two reaction zones, with the supported vanadia being contacted in one of the zones with oxygen to maintain the vanadia in its highest oxidation state, with the oxidized vanadia then being employed in the second zone for effecting conversion of the alkyl piperidine to the corresponding alkyl pyridine, with the heat released during the oxydehydrogenation providing heat requirements for the subsequent dehydrogenation in the presence of the reduced vanadia. The reduced vanadia withdrawn from the piperidine conversion zone would be recycled to the oxygen contacting step for effecting oxidation of the vanadia to a higher valence state. It is to be understood that the heat released by oxydehydrogenation could be employed to produce only a portion or none of the heat requirements for the dehydrogenation, with the remaining heat requirements (or all of the heat requirements) being provided from an external source; e.g., by an indirect heat transfer coil.

Although the conversion of alkyl piperidine to the corresponding alkyl pyridine may be effected with any one of the wide variety of supported vanadia oxidation catalysts which are known in the art, the conversion is preferably effected with a supported vanadia catalyst wherein the vanadia has been placed substantially entirely within the pores of an active support, in molten form, as described in U.S. Pat. No. 3,925,447, granted on Dec. 9, 1975. More particularly, the vanadia is present in an amount from about 25 to about 75 percent, preferably from about 30 to about 60 percent, all by weight, substantially entirely within the pores of a gamma-alumina or silica-alumina support having a surface area of greater than about 50 $M^2g/$ and a porosity greater than about 0.4 cc/g. The vanadia was placed substantially entirely within the pores of the support, in molten form, by a fusion technique, as described more particularly in U.S. Pat. No. 3,925,447, which is hereby incorporated by reference.

In accordance with another aspect of the present invention, there is provided a process for producing nicotinonitrile from a piperidine. More particularly, a 3-alkyl piperidine, 2,3-dialkyl piperidine or a 2,5-dialkyl piperidine is converted to the corresponding pyridine by the use of a supported vanadia catalyst, as hereinabove described, with the resulting pyridine product being converted to nicotinonitrile by reaction with ammonia in the presence of a supported vanadia catalyst.

In accordance with this aspect of the present invention, the supported vanadia catalyst which is employed for both the conversion of the alkyl piperidine to an alkyl pyridine and for conversion of the alkyl pyridine to nicotinonitrile is the preferred catalyst wherein the vanadia was supported, in molten form, substantially entirely within the pores of a gamma-alumina or silica-alumina support having a surface area greater than 50 $m^2/g$ and a porosity greater than 0.4 cc/g, with the vanadia being present in the pores of the support in an amount from 25 to 75, percent by weight.

The alkyl substituted pyridine is contacted with ammonia in the vapor phase in the presence of the supported vanadia catalyst, as hereinabove described, and in the substantial absence of free (molecular) oxygen, at temperatures from about 575° F to about 930° F, preferably from about 700° F to 850° F. The vanadia is in its oxidized form and provides oxygen to the process, and is itself reduced during the process.

In accordance with a preferred aspect, the reduced supported vanadia catalyst is withdrawn from the nicotinonitrile production step, and employed for the conversion of the alkyl substituted piperidine to the corresponding pyridine, with the reduced supported vanadia catalyst from such piperidine conversion then being oxidized and regenerated by contact with an oxygen containing gas to provide a supported vanadia catalyst in its oxidized state, which is then employed for the production of nicotinonitrile.

The vanadium is reduced during the process and, accordingly, is periodically regenerated to its oxidized state by contact with oxygen.

The reaction effluent includes nicotinonitrile, as well as alkyl pyridine reaction intermediate, with the nicotinonitrile being recovered as product and the alkyl pyridine reaction intermediate being recycled to the reaction for conversion to nicotinonitrile.

The invention will be further described with respect to an embodiment thereof illustrated in the accompanying drawing, wherein:

The drawing is a simplified schematic flow diagram of a process for producing nicotinonitrile from an alkyl substituted piperidine.

Referring now to the drawing, there is shown a nicotinonitrile production reactor, schematically indicated as 10, an alkyl pyridine production reactor, which also functions as a stripper for removing volatile matter from the supported vanadia catalyst, schematically indicated as 11 and a catalyst regenerator, which functions to oxidize the supported vanadia to the oxidized valence state, schematically indicated as 12. The supported vanadia is maintained in a fluidized state in reactors 10, 11 and 12.

An alkyl piperidine feed, preferably 3-methyl or 3-ethyl piperidine, 2,3-dimethyl or -diethyl piperidine, or 2,5-dimethyl, diethyl or methyl/ethyl piperidine, in line 13, is introduced into the piperidine production reactor 11 wherein the piperidine is contacted with the reduced supported vanadia catalyst introduced into reactor 11 through line 14 to convert the alkyl substituted piperidine to the corresponding alkyl substituted pyridine. A stripping gas, such as, steam, nitrogen and the like, in line 15, is also introduced into the reactor 11 for the purpose of stripping volatile matter from the supported vanadia catalyst introduced through line 14.

An effluent, containing the alkyl substituted pyridine, small amounts of pyridine, unconverted alkyl substituted piperidine, hydrogen and any stripping gas introduced through line 15 is withdrawn from reactor 11 through line 16 and introduced into a separation and recovery section, schematically indicated as 17, to separate alkyl pyridine, as well as the other components from the effluent. As should be apparent, unconverted alkyl piperidine can be recycled to the reactor 11. Alternatively, the effluent from reactor 11 may be directly introduced into reactor 10; ie, without separation of components.

Alkyl pyridine, such as 3-methyl pyridine, is withdrawn from the separation and recovery section 17 through line 18 and introduced into the nicotinonitrile production reactor 10 along with fresh feed ammonia in line 19. In reactor 10, the methyl pyridine is converted to nicotinonitrile by contact with an oxidized supported vanadia catalyst introduced through line 21.

Reduced supported vanadia catalyst is withdrawn from reactor 10 through line 14 for introduction into the alkyl pyridine production reactor 11, which also functions to strip volatile matter from the catalyst.

A reaction effluent, containing nicotinonitrile, as well as unreacted 3-methyl pyridine, is withdrawn from reactor 10 through line 22 and introduced into a separation and recovery section, schematically indicated as 23, to recover the various components. Nicotinonitrile product is withdrawn from the separation and recovery section 23 through line 24, and may be employed for the production of nicotinamide or nicotinic acid. Any unreacted 3-methyl pyridine is recovered and recycled (not shown) to the reactor 10. If the effluent from reactor 11 is directly introduced into reactor 10, recovered unreacted piperidine starting material can be recycled from section 23 to reactor 11 or alternatively recycled to reactor 10 with the unreacted methyl pyridine.

The reduced supported vanadia catalyst withdrawn from reactor 11 through line 25 is introduced into the regenerator 12 wherein the supported vanadia is contacted with molecular oxygen introduced through line 26 to effect regeneration of the supported vanadia by oxidation thereof to its oxidized valence state; namely, vanadium pentoxide. The oxidized supported vanadia is withdrawn from regenerator 12 through line 21 and introduced into the nicotinonitrile production reactor 10.

Although the present invention has been particularly described with respect to a process for producing nicotinonitrile from an alkyl piperidine, as hereinabove noted, the present invention is also applicable to producing a pyridine from a piperidine by the use of a supported vanadia catalyst, either in oxidized or reduced form, with or without subsequent production of a nitrile from the pyridine product.

The invention will be further described with respect to the following examples; however, the scope of the invention is not to be limited thereby.

EXAMPLE I

In the following runs, the catalyst was reduced 40 weight percent vanadia supported, by fusion, substantially entirely within the pores of a silica-alumina support having a surface area of greater than 50 m²/g and a porosity greater than 0.4 cc/g (Grace-135). Four hundred (400) grams of the catalyst was employed in a fluid bed reactor.

TABLE

| Run Number | 1 | 2 | 3 |
|---|---|---|---|
| Operating Conditions | | | |
| Temperature, ° F | 800 | 800 | 800 |
| Pressure | 1 atm. | 1 atm. | 1 atm. |
| Feed Composition (mole %) | | | |
| 3-Methylpiperidine | 12.45 | 11.76 | 11.76 |
| $N_2$ | 87.55 | 88.24 | 88.24 |
| Run Duration (min.) | 75 | 90 | 60 |
| Space Velocity (hr$^{-1}$) | | | |
| GHSV | 491.2 | 486 | 486 |
| LHSV | 0.3 | 0.3 | 0.3 |
| Material Balance (mole %) | 72.80 | 77.22 | 83.58 |
| Selectivities (normal) | | | |
| β-Picoline | 93.49 | 93.63 | 94.14 |
| Pyridine | 3.09 | 4.31 | 1.43 |
| Unknown | 1.44 | — | 2.00 |
| $CO_2$* (methylpiperidine equiv.) | 1.98 | 2.20 | 2.43 |
| Conversion | 86.12 | 90.00 | 93.94 |

*$CO_2$ collected on regeneration of catalyst after indicated run time.

EXAMPLE II

In this experiment a circulating fluid bed reactor system is used. The system consists of three 1 inch dia. ×4 foot reactors, each containing 400 g. of the catalyst used in Example I, with provision for circulating catalyst between them. One reactor is used for conducting the ammonolysis reaction, one for conducting the dehydrogenation reaction and one for regenerating the catalyst. Catalyst is circulated from the regenerator to the ammonolysis reactor, then to the dehydrogenation reactor, and finally back to the regenerator, completing the cycle. Feed to the dehydrogenation reactor consists of 3-methyl piperidine and nitrogen. The effluent from this reactor is combined with ammonia and fed to the ammonolysis reactor. Air is fed to the regenerator. Operating conditions and results are shown in Table II.

TABLE II

| | |
|---|---|
| Operating Conditions | |
| Temperatures, ° F | |
| Dehydrogenation | 800 |
| Ammonolysis | 750 |
| Regeneration | 900 |
| Pressure, atm. | 1 |
| Catalyst Circulation Rate, g/hr. | 4000 |
| Feed to Dehydrogenation, moles/hr. | |
| 3-Methyl Piperidine | 1.64 |
| $N_2$ | 12.31 |
| Feed to Ammonolysis, g. moles/hr. | |
| Dehydrogenation Reactor Effluent | (not measured) |
| Ammonia | 4.46 |
| Feed to Regenerator, g. mols/hr. | |
| Air | 14.0 |
| Gas Hourly Space Velocity, hr$^{-1}$ (all reactors) | 500 |
| Selectivities, mole%$^{(a)}$ | |
| Nicotinonitrile | 47.7 |
| β-Picoline | 37.2 |
| Pyridine | 3.3 |
| Unknown | 2.9 |
| $CO_2$ | 8.9 |
| Methyl Piperidine Conversion, % | 100 |

TABLE II-continued

| | |
|---|---|
| Ultimate Yield of Nicotinonitrile, mole%$^{(b)}$ | 79.3 |

$^{(a)}$Approximately 50% of the hydrogen generated on dehydrogenation was oxidized to water during ammonolysis. $^{(b)}$Since β-picoline can be recycled, ultimate yield is calculated as nicotinonitrile selectiviey +0.85 (β-picoline selectivity). This assumes a 15% loss of β-picoline on recycle.

Numerous modifications and variations of the present invention are possible in light of the above teachings and, therefore, within the scope of the appended claims, the invention may be practiced otherwise than as particularly described.

What is claimed is:

1. A process for producing nicotinonitrile, comprising:
    a. converting in a first reaction zone a member selected from the group consisting of 3-alkyl piperidines, 2,3-dialkyl piperidines, and 2,5-dialkyl piperidines to the corresponding pyridine by contacting said member with supported vanadia as a catalyst, at a temperature of from 500° F to 1000° F, said supported vanadia containing from about 25 to about 75 percent, by weight, of the vanadia, said vanadia having been placed in molten form substantially entirely within the pores of the support, the support having a surface area greater than about 50 m²/gm and a porosity greater than about 0.4 cc/gm, said support being selected from the group consisting of gamma-alumina and silica-alumina; and
    b. contacting said corresponding pyridine in a second reaction zone with ammonia at a temperature of from 575° F to 930° F in the presence of oxidized vanadia supported on a porous support to produce nicotinonitrile, said support containing from about 25 to about 75 percent, by weight, of the vanadia having been placed in molten form substantially entirely within the pores of the support, the support having a surface area greater than about 50 m²/gm and a porosity greater than about 0.4 cc/gm, said support being selected from the group consisting of gamma-alumina and silica-alumina.

2. A process for converting an alkyl piperidine to the corresponding alkyl pyridine, comprising:
    contacting the alkyl piperidine with supported vanadia at a temperature of from 500° F to 1000° F to effect conversion thereof to the corresponding alkyl pyridine, said supported vanadia containing of from about 25 to about 75 percent, by weight, of the vanadia, said vanadia having been placed in molten form substantially entirely within the pores of the support, the support having a surface area greater than about 50 meters square per gm. and a porosity greater than about 0.4 cc per gm., said support being selected from the group consisting of gamma-alumina and silica-alumina.

3. The process of claim 2 wherein the conversion is effected in the absence of molecular oxygen.

4. The process of claim 3 wherein the supported vanadia catalyst is maintained in fluidized form.

5. The process of claim 4 wherein the alkyl substituted piperidine is selected from the group consisting of 3-alkyl piperidines, 2,3-dialkyl piperidines and 2,5-dialkyl piperidines.

6. The process of claim 4 wherein the piperidine is 3-methyl piperidine and the corresponding pyridine is 3-methyl pyridine.

7. The process of claim 4 wherein the catalyst is periodically regenerated by direct contact with molecular oxygen.

8. The process of claim 2 wherein supported vanadia from step (b) is passed to step (a) and supported vanadia is contacted with molecular oxygen to effect regeneration thereof subsequent to step (a) and regenerated supported vanadia is passed to step (b).

9. The process of claim 8 wherein said member in step (a) is 3-methyl piperidine.

10. The process of claim 8 wherein the contacting of steps (a) and (b) are effected in the absence of molecular oxygen.

11. The process of claim 10 wherein an effluent containing the corresponding alkyl pyridine is withdrawn from the first reaction zone and is introduced into the second reaction zone without separation of components.

* * * * *